United States Patent
Axelrod et al.

(10) Patent No.: US 8,170,673 B2
(45) Date of Patent: May 1, 2012

(54) CARBON NANO-TUBE POWER CELL

(75) Inventors: Noel Axelrod, Jerusalem (IL); Amir Lichtenstein, Tel Aviv (IL); Eran Ofek, Modi'in (IL)

(73) Assignee: Physical Logic AG, Zug (CH)

( * ) Notice: Subject to any disclaimer, the term of this patent is extended or adjusted under 35 U.S.C. 154(b) by 959 days.

(21) Appl. No.: 12/139,589

(22) Filed: Jun. 16, 2008
(Under 37 CFR 1.47)

(65) Prior Publication Data
US 2010/0036450 A1    Feb. 11, 2010

Related U.S. Application Data

(60) Provisional application No. 60/944,515, filed on Jun. 17, 2007.

(51) Int. Cl.
*A61N 1/04*    (2006.01)
(52) U.S. Cl. ............. 607/35; 607/34; 977/742; 977/752
(58) Field of Classification Search .......... 977/742–752; 607/35
See application file for complete search history.

(56) References Cited

U.S. PATENT DOCUMENTS

| | | | |
|---|---|---|---|
| 4,621,225 | A | 11/1986 | Birk |
| 6,559,550 | B2 | 5/2003 | Herman |
| 6,718,834 | B1 | 4/2004 | Sood et al. |
| 6,921,575 | B2 | 7/2005 | Horiuchi et al. |
| 2005/0049555 | A1 | 3/2005 | Moorehead et al. |

OTHER PUBLICATIONS

S. Ghosh, A. K. Sood, S. Ramaswamy, and N. Kumar; Flow-induced voltage and current generation in carbon nanotubes, Physical Review B 70, 205423, 2004.
A Carbon Nanotube Film for Power Harvesting, Key Engineering Materials vols. 326-328 (2006) pp. 1447-1450, Inpil Kang, Gyung Rak Choi2,, Joo Yung Jung, Yong Hoon Chang, Yeon-Sun Choi, Mark J. Schulz.

*Primary Examiner* — Niketa Patel
*Assistant Examiner* — Joseph Stoklosa
(74) *Attorney, Agent, or Firm* — Mark M Friedman (57) ABSTRACT

A device which converts mechanical deformation in electrical current, these mechanical deformations are generated as a result of liquid pressure over a part of the device. This device is integrated within an implantable lead and inserted into the cardiovascular system of a patient. The purpose of the device is to charge a battery which stores energy for various uses of other implantable devices.

20 Claims, 11 Drawing Sheets

CARBON NANO-TUBE POWER CELL

CROSS REFERENCE TO RELATED APPLICATIONS

The present application claims priority to U.S. provisional patent application having Ser. No. 60/944,515, titled "Carbon Nano-tube Power Cell", that was filed 17 Jun. 2007, which is incorporated herein by reference

BACKGROUND OF INVENTION

The present invention relates to a miniature power generating device suitable for implantation so as to generate power required by implanted medical devices.

While implantable medical devices, such as Pacemakers, ICD's and other grow in increasing sophistication, they all require a source of power. It is most convenient for the patient to implant a battery with the device to avoid the needs for leads to an external power source, which can be a source of infection, inflammation and the like. However, batteries have a limited life requiring eventual replacement, and or placing design constraints on the device power consumption and hence functionality such that it is much less than what might be achieved with a non-invasive device.

Hence there is a need for high density and high efficiency power generating cell that is bio-compatible for implantable medical device that either replaces or supplements a battery, being powered off energy generated by or available from the living organism.

SUMMARY OF INVENTION

In the present invention, the first object is achieved by providing a plurality of metallic carbon nanotubes (multi-walled or single walled) in contact with opposing electrodes in fluid communication between two flexible reservoirs containing an electrolytic fluid At least about a portion of one of the two lobes that forms the dumb bells shaped device is in tactile communication with the blood, such that each pulse causes repeated contraction and hence pumping of the contained fluid through the carbon nano-tubes or channels to produce a charge.

The above and other objects, effects, features, and advantages of the present invention will become more apparent from the following description of the embodiments thereof taken in conjunction with the accompanying drawings.

DETAILED DESCRIPTION

Referring to FIGS. 1 through 11, wherein like reference numerals refer to like components in the various views, there is illustrated therein a new and improved Carbon Nano-tube Power Cell, generally denominated 100 herein.

Conductive carbon nanotubes also known as metallic carbon nanotubes (MNT) either multiwalled (MWNT) or single walled (SWNT) in contact with flowing liquid provide a unique micro-fluidic system that offers a large interfacial area of intimate atomic contact between the liquid and the solid substrate. This can lead to a strong coupling of the free charge carriers in the nano-tube to the particles in the flowing liquid, more so if the liquid is polar or ionic in nature.

The effect of this coupling is expected to be further enhanced due to charge carrier entrainment because of the quasi-one dimensionality of the conducting nano-tubes. The effect of flow induced current in MWNT was shown by Kral P & Shapiro, 2001, Phys. Rev. Lett, 86, 131 Recently, the flow of a variety of liquids over SWNT bundles was experimentally studied, and was found to generate voltage in the sample along the direction of the flow as taught by S. Ghosh, A. K. Sood, S. Ramaswamy, and N. Kumar; Flow-induced voltage and current generation in carbon nanotubes, Physical Review B 70, 205423, 2004, which is incorporated herein by reference.

Quite unexpectedly, however, the dependence of the voltage on the flow speed was found to be nonlinear, and could be fitted to a logarithmic form over five decades of the variation of the speed.

Figure 1:
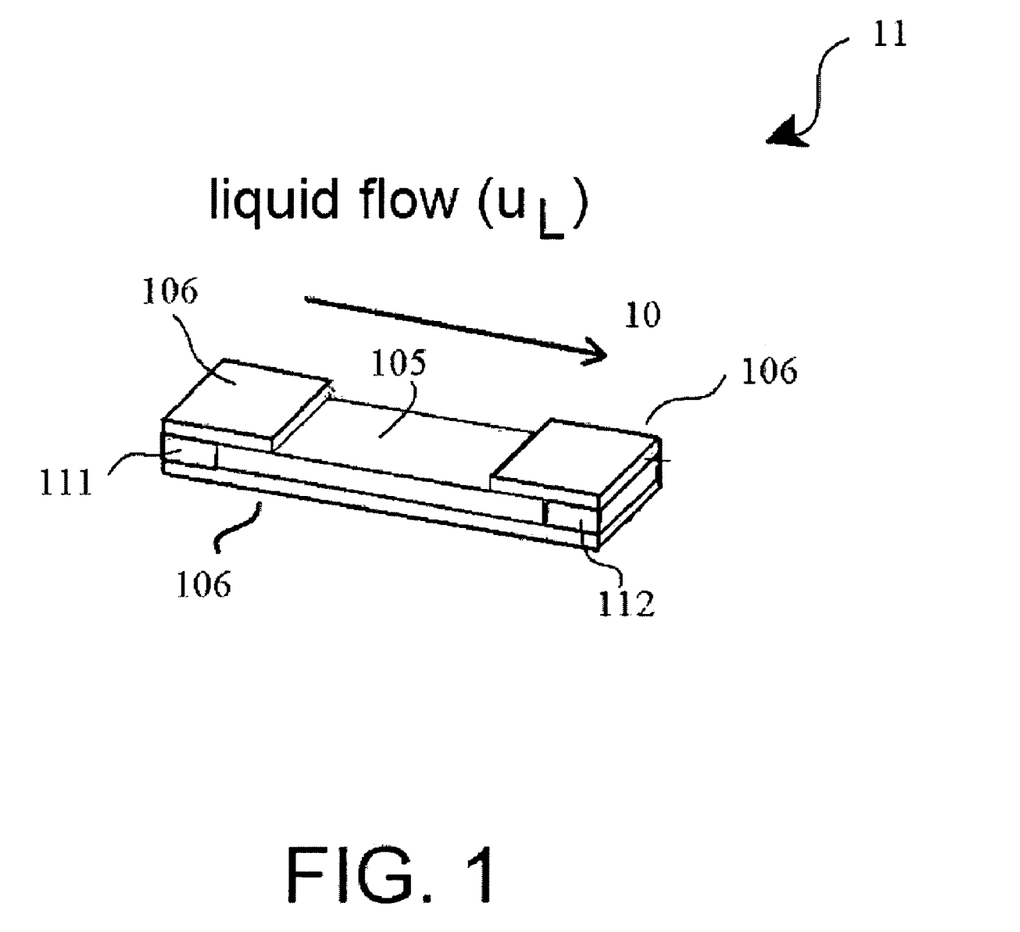
FIG. 1 is a schematic illustration of the flow with respect to the metallic nanotubes and electrodes in a portion of the nano-tube portion of device 100.

FIG. 1 is a schematic illustration of the nano-tube portion 11 of device 100 that utilizes the teaching of Ghosh et al. which can also be used as an experimental setup for measuring of the electrical current and voltage. SWNT bundles 105 prepared by arc discharge method are placed between two metal electrodes 111 and 112. The nanotubes 105 are kept in their place by a supporting insulating substrate 106. The same insulator 106 is also shown as being applied as a superstrate on the portion of the nanotubes 105 covered by electrodes 111 and 112. This configuration is preferable in particular for stacking portions 11 as shown in FIG. 6. The electrical signal is measured along the flow direction ($u_L$) as shown in FIG. 1 by arrow 10.

The dependence of flow induced voltage and current fits to the empirical relations taught by Ghosh, supra.

$$U = U_0 \log\left(\frac{u}{v_0} + 1\right) \quad (1)$$

$$I = I_0 \log\left(\frac{u}{v_0} + 1\right) \quad (2)$$

Where $v_0$ is the reference flow velocity, u is the flow velocity, $I_0$ is the initially measured electrical current, $U_0$ is the initially measured voltage. Please note that both $I_0$ and $U_0$ are constant.

In experiments of others 1 M NaCl aqueous solution was used, this results in the flow induced voltage of $U_0$=30 mV for $v_0$=5×10$^{-4}$ m/s and $$R_0 = \frac{U_0}{I_0} = 75$$

Ω at L=0.5 cm, H=2 cm, h=70 μm.

The total volume of the nanotube film was $V_0$=7 mm$^3$.
The flow-induced power is given by the formula $$P = IU = \frac{U_0^2}{R_0}\left(\log\left(\frac{u}{v_0}+1\right)\right)^2 \quad (3)$$

The power generated per unit volume of the carbon nanotube film is $W=P/V_0$.

For example if u=1 cm/sec, then P=0.11 mW or W=16 μW/mm$^3$. So, if for example the active volume of the device is 1 cm$^3$, then the power of 16 mW could be generated. The maximum power that can be used for charging a battery is half of that value.

Figure 2:
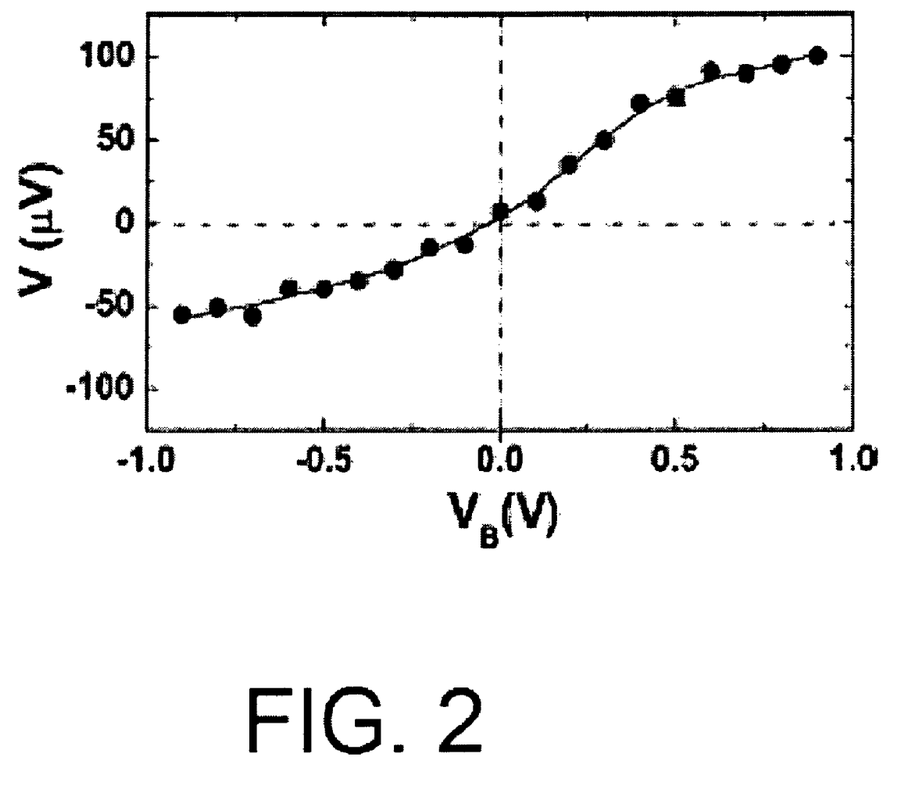
FIG. 2 is a graph of flow induced voltage as a function of bias voltage for a prior art carbon nano-tube assembly.
Figure 3:
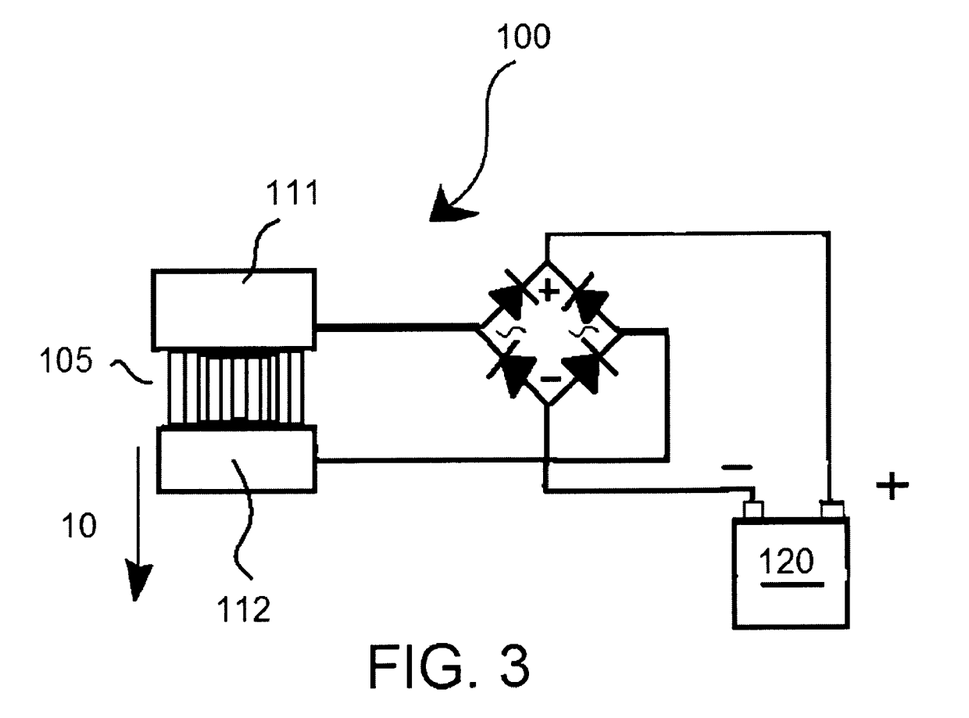
FIG. 3 is a representative charging circuit for device 100.

Ghosh et al. also considered the direction of the flow induced current with respect to the flow direction as a function of the bias voltage $V_B$ (as shown in FIG. 2 of the Ghosh reference, reproduced herein as FIG. 2). This potential biases the SWNT with respect to the Au-reference electrode immersed in the flow chamber close to the sample as shown in the inset of FIG. 2. The dependence of the sign and the magnitude of the flow-induced voltage on $V_B$ for an aqueous solution of 0.01 M KCl (conductivity 1.4 mS/m) and for a fixed flow speed of 0.04 cm/s are shown in FIG. 3. It is seen that the flow-induced signal is positive, i.e., I is anti-parallel to u when $V_B$ is positive, and the sign of the signal is reversed, i.e., I is parallel to u, when $V_B$ is negative.

Thus, for the current I to be parallel, (antiparallel) to u, the charge carriers in the nanotubes need to be holes (electrons).

When the nanotubes are biased positively, the anions Cl$^-$, OH$^-$ move closer to the SWNT, localizing holes on the carbon and making electrons available for flow-induced current. Similarly, holes are liberated when the bias is negative. As the bias voltage is increased the number of carriers participating in the flow induced current will increase as shown in FIG. 3.

In the experiment above the voltage increases more than 50 times for $V_B$=0.5 V. Assuming that the power consumption by biasing the nano-tube film is much smaller than the power generated by the film itself we could write the maximum power generated from a unit volume of the carbon nano-tube film as:

$$W_{max} = G^2 \frac{U_0^2}{R_0}\left(\log\left(\frac{u}{v_0}+1\right)\right)^2 \quad (4)$$

Where G is the gain factor due to the biasing effect, For u=1 cm/sec and G=50 we get $W_{max}$=20 mW/mm$^3$ of the device.

FIG. 3 is an electrical schematic diagram of the described flow induced power cell device 100. As can be seen in FIG. 3 above, the device 100 described in FIG. 1, has opposing electrodes 111 and 112 connected to opposing sides of diode bridge 110, which is in turn connected to a battery 120 via the 2 remaining sides of diode bridge 110. Thus, regardless of the direction of the electron flow (electrical current) between electrodes 111 and 112, the current from the bridge 110 will always flow to charge the battery 120.

Figure 4:
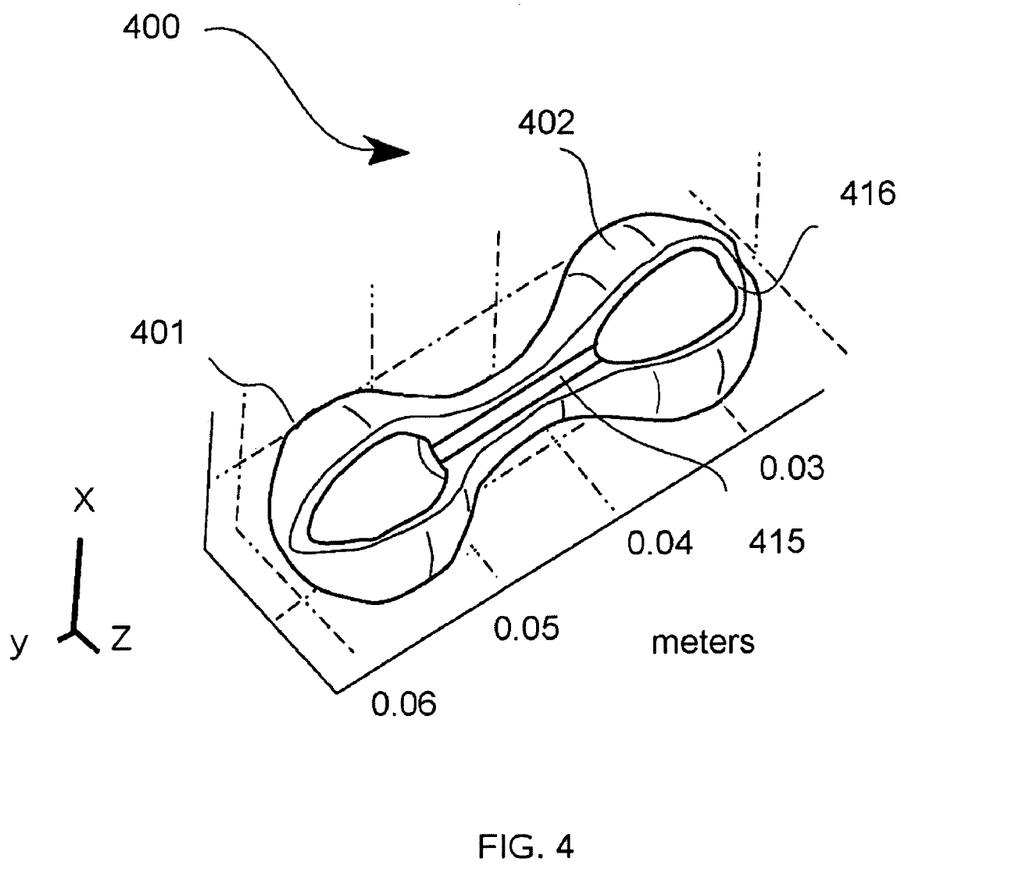
FIG. 4 is a partially cut away perspective view of a portion of the flow cell 400 of device 100.

FIG. 4 illustrates a schematic model of the flow cell 400 portion of the device 100, which is optionally deployed as shown in other embodiments as an invasive, implantable power harvesting device. Flow cell 400 provides a means for the periodic flow of fluid that preferably contains ions, such as the aqueous KCl solution described above, over the nanotube portion and electrodes shown in FIG. 1. This model simulates the flow dynamics of liquids. The structure is comprised of an elastic, hermetically sealed, polymer shell (which is bio-compatible) composed of materials such as silicon, nylon etc.

Flow cell 400 preferably has a general dumb bell type shape as shown with each end being a substantially spherical or elliptical chamber or lobes, 401 and 402 the opposing chambers or lobes separated by a narrow neck or channel 415 containing the MNT's. As shown in FIG. 4 this device 400 is inserted into a lead in such a way that one of the lobes of the device is exposed to the blood and the other side is left unexposed (positioned within the lead). The inner part 410 of the connected lobes 401 and 402 of device 400 is filled with an ionized liquid, such as aqueous solutions of various salts. Flow cell 400 may have other shapes than the dumbbell illustrated herein.

In the examples given, the wall 416 of the shell has a thickness of about 1.25 mm at the thinnest portion near the apex most distal from the channel 415 between the lobes. However, it should be appreciated that the wall thickness can be varied depending on the compliance of the material it is constructed from.

Pressure exerted over the exposed section or lobe of the flow cell 400 of device 100, causes that part or lobe to contract, pushing the liquid within over the single walled carbon nano tubes (positioned in the center of the device—in darker grey), and expand the un-exposed section of the device. This flow of liquid over the single walled carbon nano tubes generates the electrical current required to charge the battery (the explanation regarding this physical phenomenon is described in greater detail above).

Figures 5A, 5B:
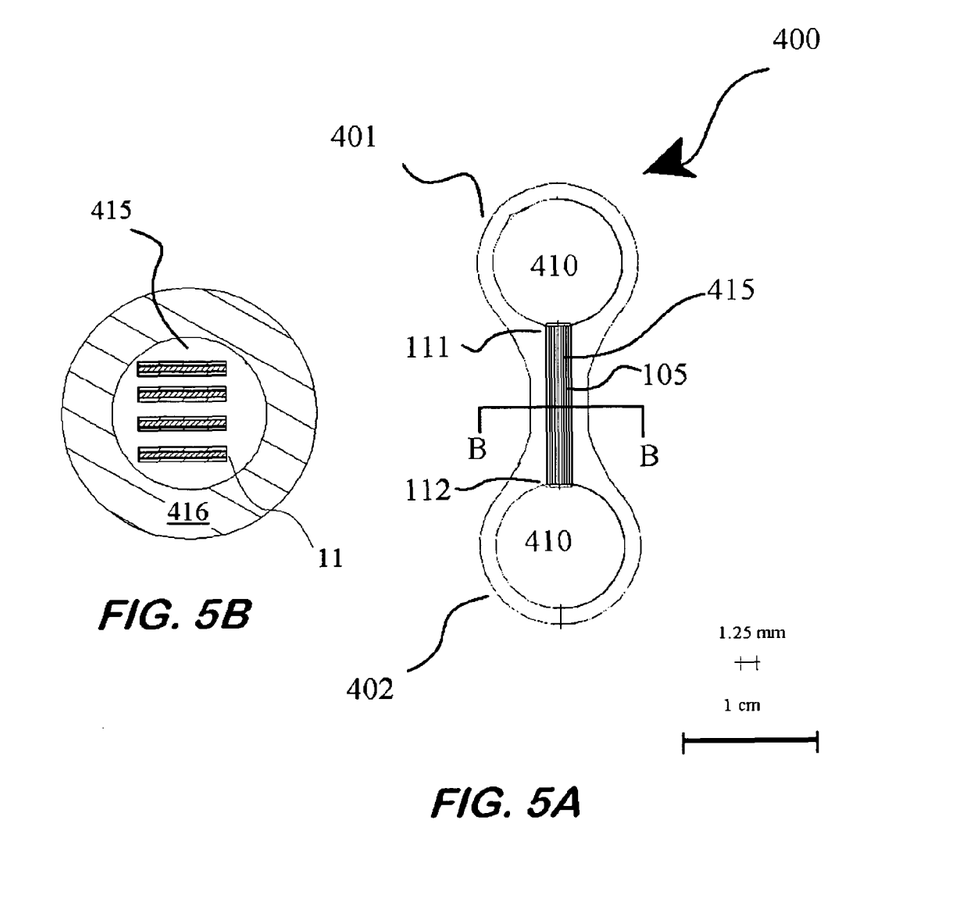
FIG. 5 is a cross-sectional elevation through the flow cell portion of the device 100 shown in FIG. 5.

FIG. 5 illustrates a cross-sectional view of the device described in FIG. 4, the black section in the middle of the device contains the single walled carbon nano tubes, and the two "empty" holes at each side of the device contain the liquid which flows from one lobe of the device to the other. Two electrical leads are connected to two electrodes (in contact with the carbon nano tubes); please note that these electrodes do not interfere with the flow of liquid from one side of the device to the other and vice versa.

Figures 6A, 6B:
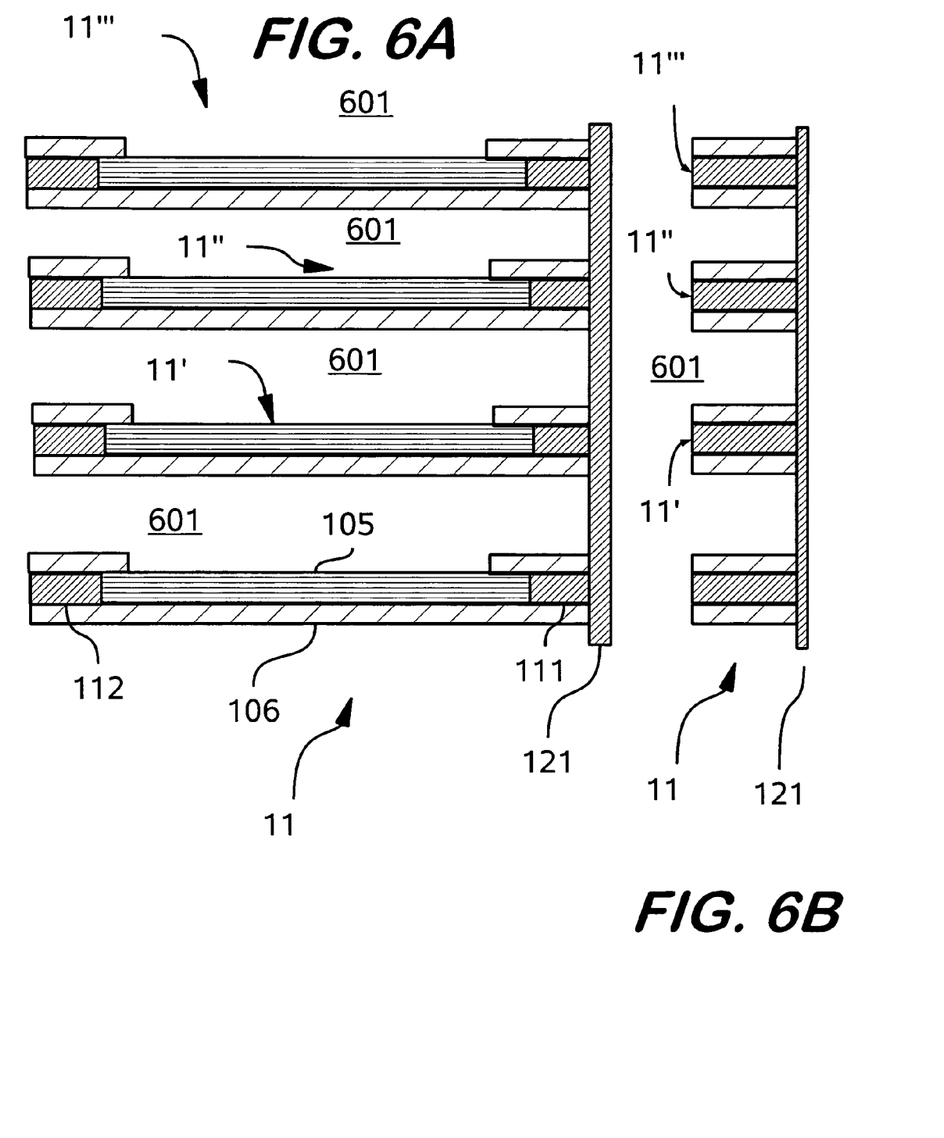
FIG. 6 is a perspective cut away view of the carbon nano-tube portion of in the narrow waste section between the opposing fluid chamber in FIG. 5.

FIGS. 6A and 6B illustrate one embodiment of the internal organization of the single walled carbon nano tubes in the device. FIGS. 6A and 6B are orthogonal sections of the stack of MNT films 105 and associated electrodes 111 and 112, each forming device sub portions 11 of FIG. 1, being labeled 11, 11', 11" and 11 '" in this FIG. The common electrodes 111 of sub portions 11, 11', 11" and 11'41, are connected in parallel via a bus electrode 121 for the common electrodes 111. Another common bus would connect the opposite electrodes 112. This stacked arranged provides subchannels 601 so that liquid can flow between each of lobes 401 and 402 of the fluid reservoir 400 of MNT device 100. The nano tubes are preferably organized in a thin film structure, (several tens of microns thick) and are anchored to substrate 106 using various metals which act as the electrodes. On top of the electrodes another dielectric layer is deposited. This structure constitutes a single film or device portion 11.

Figure 9:
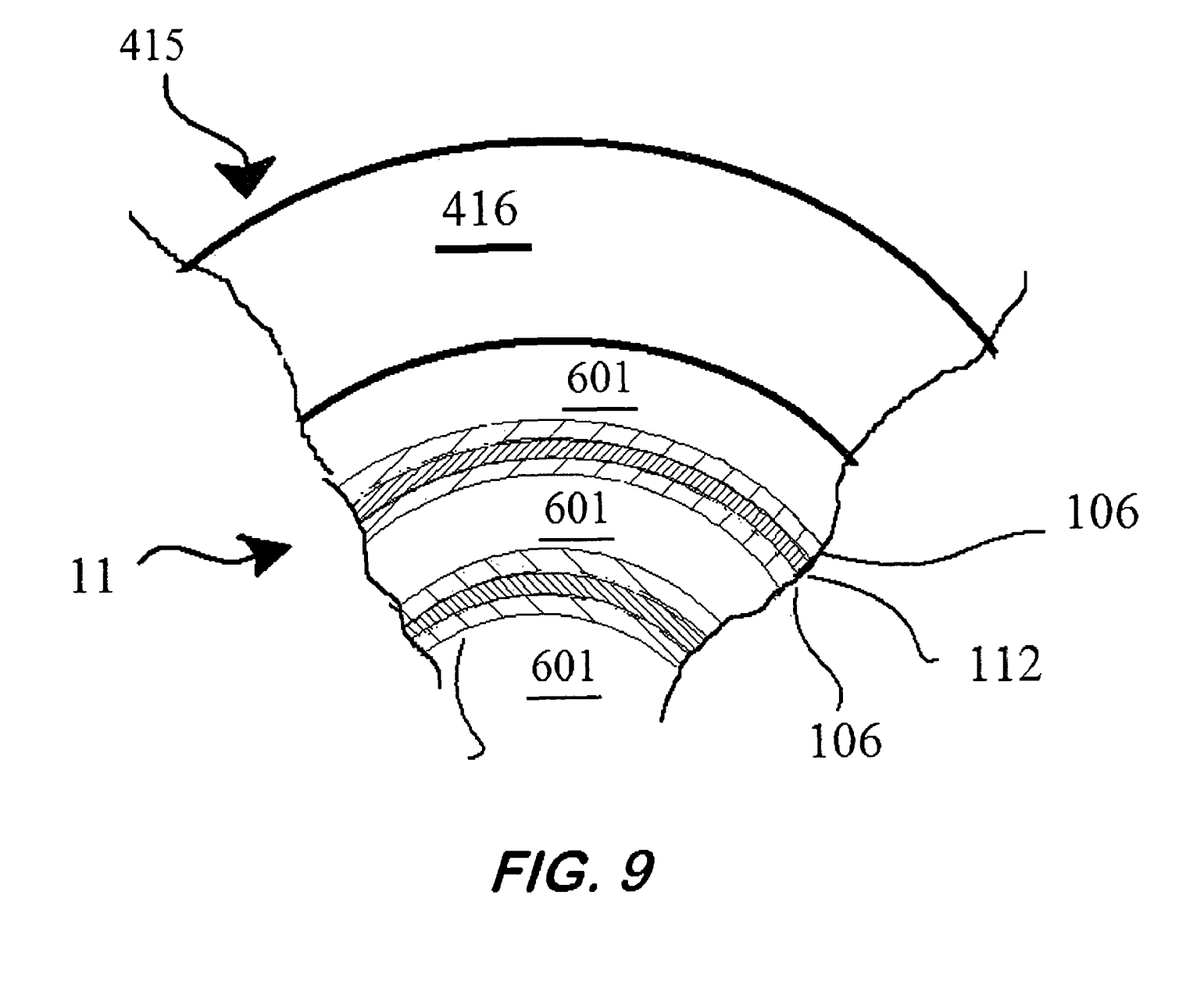
FIG. 9 is a cross-section of a the central portion of another embodiment of the device.

It should also be appreciated that a similar series of alternating channels between each layer of MNT and their respective electrodes 111/112 and a support substrate 106 can be forms in a essentially concentric arrangement formed by the helical rolling of a layer of MNT and electrodes disposes on a flexible substrate, as shown in section in FIG. 9, which is a section through a portion of channel 415. In such a configuration a single wide sub-portion 11 is rolled in a spiral. As this sectional view section is at the electrode plane 112, the nanotube layer 105 does not appear in the drawing. To the extent that the nanotube layer 105 or electrodes 111/112 are not sufficiently flexible for rolling in a spiral, the rolling or bending can be performed on stripped sub-portion of substrate 106 not coated with electrodes and nanotubes. The advantage of this configuration however is that all the electrodes are already connected in the spiral pattern. In the case of using multiple folds the electrodes, such as 121 in FIG. 6 can be added after folding.

Figure 7:
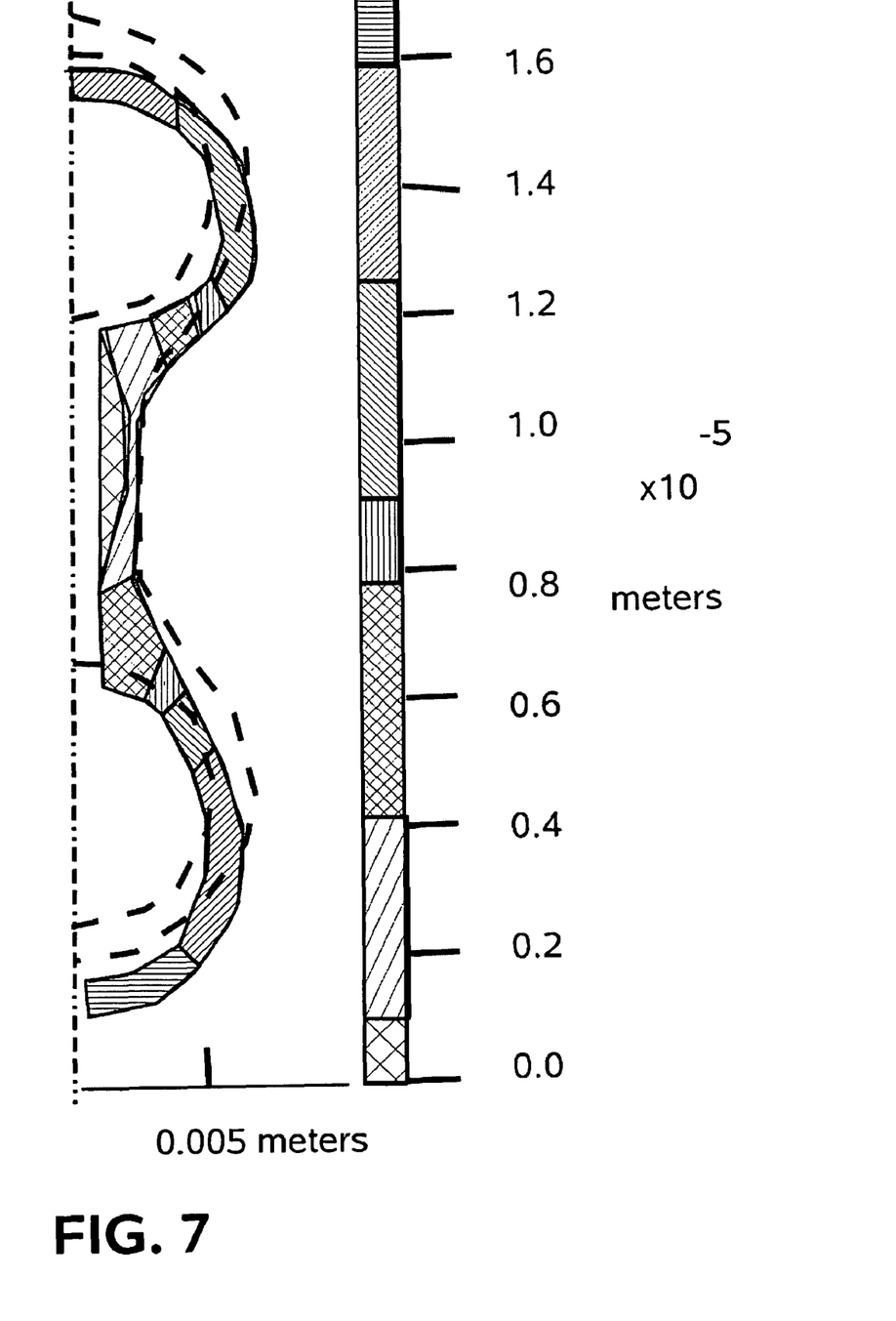
FIG. 7 are the results of a FEM model of displacement of the flexible portion of the operative devise in a 2-D plot corresponding to the section view shown in FIG. 5.

FIG. 7 illustrates the deformation of the membrane (outer shell) as described above, when pressure is exerted over the outer shell of the lower lobe (which is effectively a membrane) causing liquid flow from one lobe of the device 400 to the other, as well as the reversed flow. The grey scale on the right represents the magnitudes of the displacement as mapped onto the now distorted device 400 in grayscale. The solid outline is the undistorted or equal pressure shape of device 400. Deformation on the upper lobe results in deformation of the lower lobe, with minor deformation of the central connecting channel 415 wall. It is also apparent that volume of liquid in the bottom lobe increases as the volume in the upper lobe decreases. To the extent that such deformation in channel 415 would damage the MNT array structures or subportions 11, the wall of the central connecting channel can be thicker than shown or reinforced with more rigid materials than the lobes 401 and 402.

Figure 8:
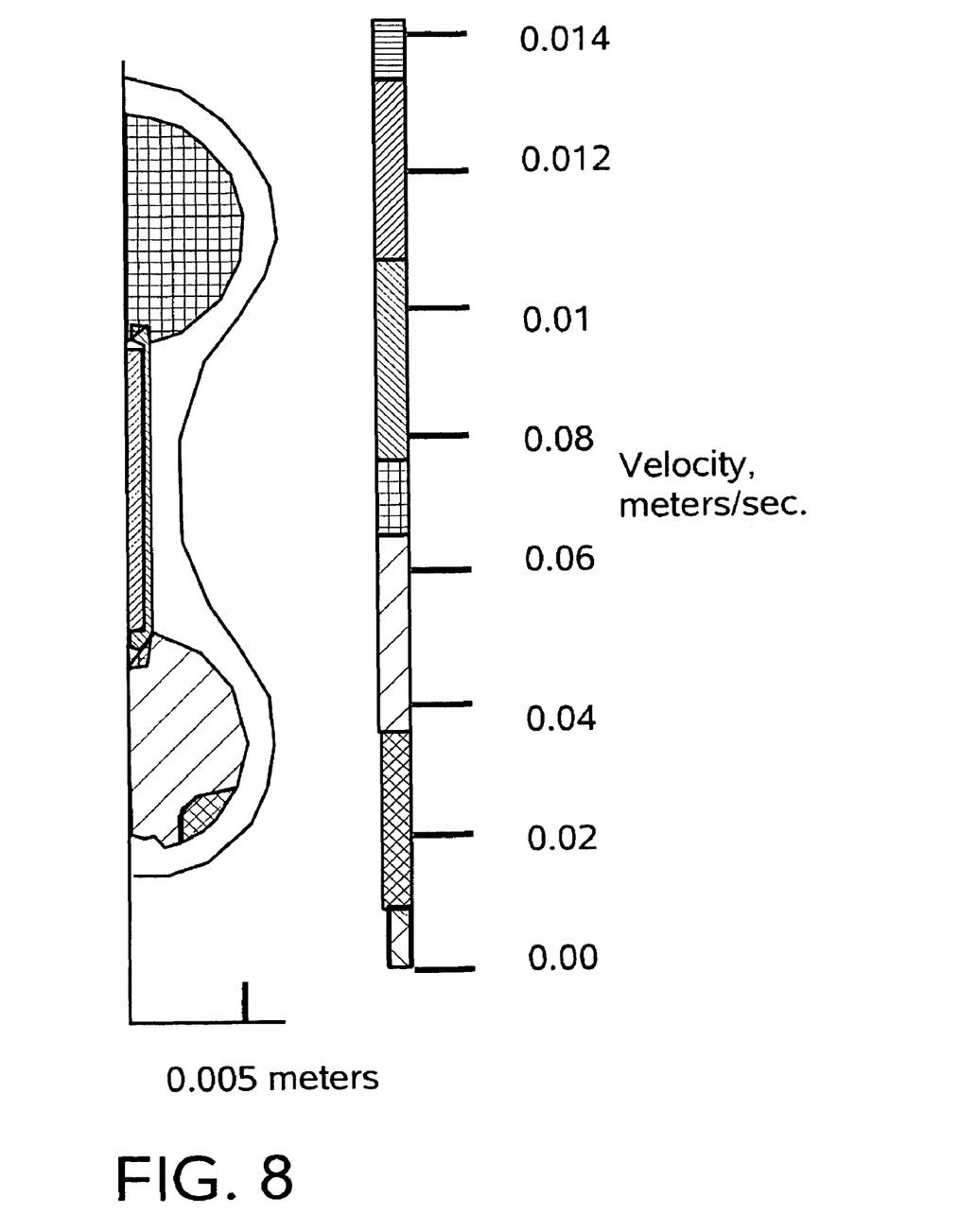
FIG. 8 are the results of a FEM model of the velocity field of the flexible portion of the operative devise in a 2-D plot corresponding to the section view shown in FIGS. 5 and 7.

FIG. 8 illustrates the velocity flow field direction by a series of overlayed short arrows, which is the distribution of the velocity of the flow within the device is illustrated. The grey scale bar on the right represent the magnitude of the velocity; the maximum velocity is measured in the middle of the channel 415 (where the nano tubes 105 are located) and is calculated to be 1.4 cm/s using Finite Element Methods.

Figure 10:
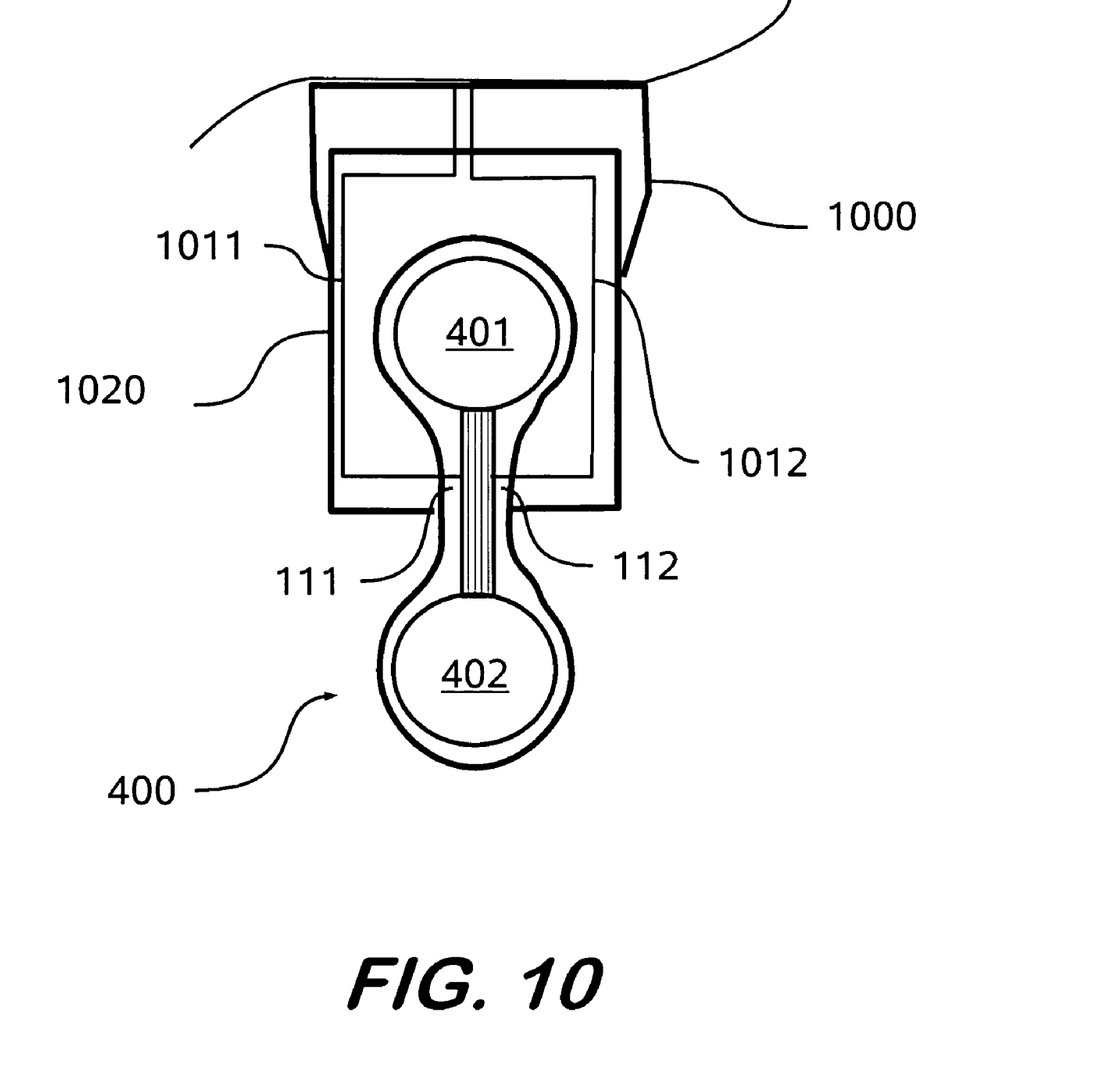
FIG. 10 is a cross-section of an embodiment wherein any of the devices of FIG. 1-9 is disposed at the end of a catheter or implanted lead.

FIG. 10 illustrates a first embodiment of a structure and method of using device 100 as power generating cell or device for implantation in a human being or other living being. The periodic pressure of the pulse causes the cyclical compression and expansion of at least one lobe to force fluid through channel 415, and hence generate current and charging battery 120. The implantation can be temporary or permanent. Preferably at least one of the lobes, in this example the upper lobe 401, is isolated from external pressure by the surrounding can 1020. In contrast, the lower lobe 402 is subjected to the periodical pressure of the blood stream, being either the end of catheter or cardiac electrode lead 1000, which supports can 1020. Device 100 has electrode leads 1011 and 1012 are connected to the electrodes 111 and 112 on opposite sides of the MNT array 105 in channel 415.

Figure 11:
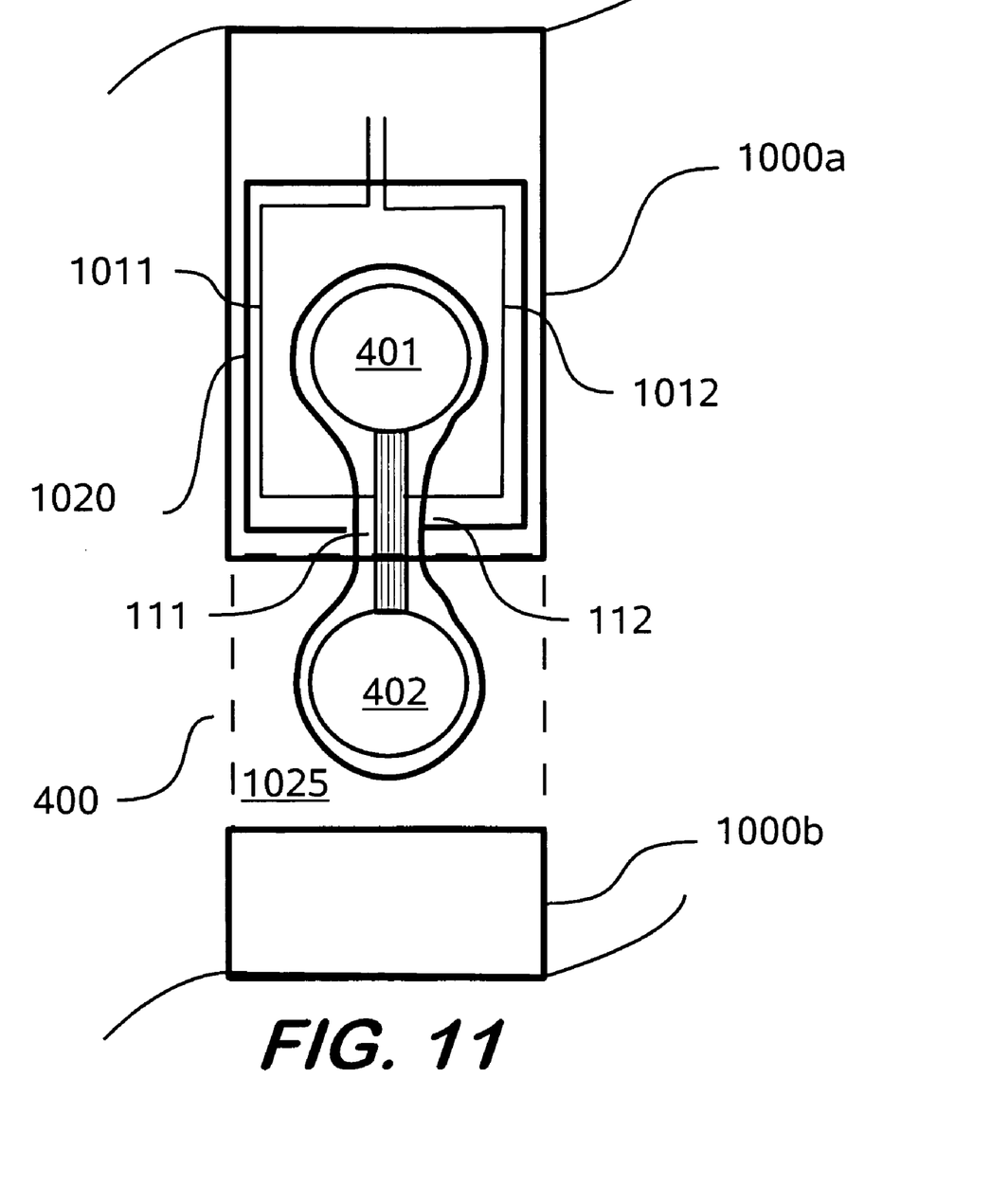
FIG. 11 is a cross-section of an embodiment wherein any of the devices of FIG. 1-9 is disposed within, for example a portion of a catheter or lead.

FIG. 11 illustrates an alternative embodiment of a structure and method of using device 100 as an implanted power cell. The catheter or lead upper portion 1000*a* contains the can 1020, below which is an open or exposed portion 1025 for lobe 402 that connects to the lower catheter or lead portion 1000*b*. However, the upper and lower portion 1000*a* and 1000*b* are connected around cavity or exposed portion. It should be understood that such exposed portion may also be a pliable membrane containing fluid that surrounds lobe 402, or the wall of lobe 402 can form a portion of the pliable portion of the catheter/lead.

The description of the use of device 100 in a catheter or lead is illustrative, as it should be appreciated that device 100, need not be in direct contact with blood, if the periodic pressure of the blood flow is transmitted to its location through other tissue or fluid.

While the invention has been described in connection with a preferred embodiment, it is not intended to limit the scope of the invention to the particular form set forth, but on the contrary, it is intended to cover such alternatives, modifications, and equivalents as may be within the spirit and scope of the invention as defined by the appended claims.

The invention claimed is:

1. An implantable power generating device comprising:
   a) a first implantable flexible fluid confining lobe,
   b) a second implantable flexible fluid confining lobe,
   c) an implantable narrow channel of substantially lower fluid capacity than each of said first and second flexible fluid containing lobes forming a fluid communication channel there between,
   d) the narrow channel further comprising at least one layer of metallic carbon nanotubes (MNT's) selected from the group consisting of single wall nanotubes (SWNT's) and multi-walled nanotubes (MWNT's), the opposite ends thereof disposed toward the junction between said first flexible fluid confining lobe and said narrow channel and toward the junction between said second flexible fluid confining lobe and said narrow channel, and
   e) isolated electrodes with which the opposite ends of the MNTs are in electrical communication.

2. A power generating device according to claim 1 wherein said flexible fluid confining lobes are filled with an ionizable compound in solution.

3. A power generating device according to claim 1 wherein at least a portion of one lobe is exposed to period pressure variations, with the other lobe substantially isolated there from such that -(electrolyte) fluid is periodically pumped through the MNT array to generate a current or charge between the isolated electrodes.

4. A power generating device according to claim 1 further comprising a plurality of substrates for supporting the MNT's in said narrow channel in multiple stacks of MNT's disposed on said substrate leaving a plurality of intervening channels for the flow of the ionizable fluid there between.

5. A power generating device according to claim 1 further comprising at least one substrate for supporting the MNT's wherein the MNT's in said narrow channel are a spiral wound array of MNT's disposed on said substrate having intervening channels for the flow of the ionizable fluid between the layers of the spiral winding.

6. A power generating device according to claim 1 wherein said a first flexible fluid confining lobe, a second flexible fluid confining lobe and said narrow channel of substantially lower fluid capacity than each lobes in fluid communication there between have a dumbbell shape.

7. A power generating device according to claim 1 wherein said a first flexible fluid confining lobe, a second flexible fluid confining lobe are pliable polymeric membranes.

8. A power generating device according to claim 7 wherein narrow channel of substantially lower fluid capacity has a more rigid wall that the pliable polymer members of said a first flexible fluid confining lobe and second flexible fluid confining lobes.

9. A power generating device according to claim 7 wherein narrow channel of substantially lower fluid capacity has a thicker wall than the pliable polymer members of said a first flexible fluid confining lobe and second flexible fluid confining lobes.

10. An implantable power generating device comprising:
   a) a first implantable flexible fluid confining lobe,
   b) a second implantable flexible fluid confining lobe,
   c) an implantable narrow channel of substantially lower fluid capacity than each lobes in fluid communication there between,
   d) a can having disposed therein one of said first and second flexible fluid confining lobes, the can providing pressure isolation of said lobe enclosed therein from the surrounding environment,
   e) a catheter or lead for supporting at least one of said flexible lobes, said narrow channel and said can, wherein the other lobe not disposed in said can is at least indirectly exposed to the external environment of said catheter,
   f) wherein said flexible fluid confining lobes are filled with an ionizable compound in solution,
   g) the narrow channel further comprising at least one layer of metallic carbon nanotubes (MNT's), the opposite ends thereof disposed toward the junction between said first flexible fluid confining lobe and said narrow channel and toward the junction between said second flexible fluid confining lobe and said narrow channel, and
   h) isolated electrodes with which the opposite ends of the MNTs are in electrical communication,
   i) whereby the period pressure variation on the lobe not disposed in said can, causes the periodic pumping of the ionizable solution past the at least one layer of the MNT's generate a current or charge between the isolated electrodes.

11. A implantable power generating device according to claim 10 wherein the other lobe not disposed in said can is directly exposed to the external environment of said catheter.

12. A implantable power generating device according to claim 10 wherein the other lobe not disposed in said can is disposed at the end of the catheter or lead.

13. A implantable power generating device according to claim 10 wherein the other lobe not disposed in said can is disposed between the end of said catheter or lead.

14. A implantable power generating device according to claim 10 further comprising at least one substrate for supporting the MNT's wherein the MNT's in said narrow channel are a spiral wound array of MNT's disposed on said substrate having intervening channels for the flow of the ionizable fluid between the layers of the spiral winding.

15. A implantable power generating device according to claim 10 further comprising a plurality of substrates for supporting the MNT's in said narrow channel in multiple stacks of MNT's disposed on said substrate leaving a plurality of intervening channels for the flow of the ionizable fluid there between.

16. A implantable power generating device according to claim 10, and further comprising:
   a) a battery,
   b) a diode bridge,
   c) wherein the isolated electrodes at the first and second opposing terminals of said MNT flow cell are in signal communication with opposing terminals of said diode bridge, and the remaining 2 terminals of said diode bridge being connected to said battery whereby the flow of fluid over said MNT flow cells results in the charging of said battery.

17. An implantable charging circuit comprising:
   a) a battery,
   b) a diode bridge,
   c) an implantable metallic wall nanotube (MNT) flow cell having first and second opposing terminals,
   d) wherein the first and second opposing terminals of said MNT flow cell are in signal communication with opposing terminals of said diode bridge, and the remaining 2 terminals of said diode bridge are connected to said battery whereby the flow of fluid over said MNT flow cells results in the charging of said battery.

18. A charging circuit according to claim 17 wherein at least one of the first and second opposing terminal is externally biased.

19. A charging circuit according to claim 17 wherein said MNT flow cell comprises:
   a) a first flexible fluid confining lobe,
   b) a second flexible fluid confining lobe,
   c) a narrow channel of substantially lower fluid capacity than each of said first and second flexible fluid containing lobes forming a fluid communication channel there between,
   d) wherein said a first flexible fluid confining lobe, a second flexible fluid confining lobe and said narrow channel of substantially lower fluid capacity than each lobes in fluid communication there between have a dumbbell shape.

20. A charging circuit according to claim 19 wherein said a first flexible fluid confining lobe, a second flexible fluid confining lobe are pliable polymeric membranes.

* * * * *